(12) United States Patent
Daniel

(10) Patent No.: US 8,529,520 B2
(45) Date of Patent: Sep. 10, 2013

(54) MEDICAMENT DELIVERY DEVICE WITH ELECTRONIC DOSE SENSOR

(75) Inventor: Mattias Daniel, Stockholm (SE)

(73) Assignee: SHL Group AB, Nacka Strand (SE)

( * ) Notice: Subject to any disclaimer, the term of this patent is extended or adjusted under 35 U.S.C. 154(b) by 45 days.

(21) Appl. No.: 13/147,745

(22) PCT Filed: Aug. 25, 2009

(86) PCT No.: PCT/EP2009/060928
§ 371 (c)(1),
(2), (4) Date: Oct. 16, 2011

(87) PCT Pub. No.: WO2010/088973
PCT Pub. Date: Aug. 12, 2010

(65) Prior Publication Data
US 2012/0041363 A1    Feb. 16, 2012

Related U.S. Application Data

(60) Provisional application No. 61/150,377, filed on Feb. 6, 2009.

(51) Int. Cl.
*A61M 5/00* (2006.01)
(52) U.S. Cl.
USPC .......................................... 604/207; 604/208
(58) Field of Classification Search
USPC ..................... 604/65–67, 207–211
See application file for complete search history.

(56) References Cited

U.S. PATENT DOCUMENTS

2002/0188249 A1   12/2002  Landau
2004/0135078 A1    7/2004  Mandro et al.

FOREIGN PATENT DOCUMENTS

| WO | 03/103763 A1 | 12/2003 |
| WO | 2007/063342 A1 | 6/2007 |
| WO | 2007/116090 A1 | 10/2007 |
| WO | 2007/141225 A1 | 12/2007 |
| WO | 2008/037801 A1 | 4/2008 |

OTHER PUBLICATIONS

EPO, Int'l Search Report in PCT/EP2009/060928, Dec. 23, 2009.
EPO, Written Opinion in PCT/EP2009/060928, Dec. 23, 2009.

*Primary Examiner* — Theodore Stigell
(74) *Attorney, Agent, or Firm* — Potomac Patent Group PLLC

(57) ABSTRACT

The present invention relates to a medicament delivery device comprising a generally elongated housing comprising a distal and a proximal housing part having opposite distal and proximal ends; a medicament container coaxially arranged within said proximal housing part; drive means (18, 20, 22, 23, 30, 32) arranged to act on said medicament container for expelling a dose of medicament; and an electromechanical dose setting mechanism interactively connected to said drive means; wherein said electromechanical dose setting mechanism comprises a manually operable dose setting button (38); a dose setting member (34) comprising sensors (42) and arranged to be linearly displaced a predetermined distance along a linear path when the dose setting button is manually operated; and a printed circuit board (44) having a code sensing area (46) along the linear path of movement of the sensors, and wherein the sensors are arranged adjacent said code sensing area, such that a value of the immediate position of the dose setting member is determined and displayed as a dose value by electronic components on the printed circuit board.

7 Claims, 4 Drawing Sheets

MEDICAMENT DELIVERY DEVICE WITH ELECTRONIC DOSE SENSOR

TECHNICAL AREA

The present invention relates to a medicament delivery device having an electromechanical dose setting mechanism.

TECHNICAL BACKGROUND

There are a number of medicament delivery devices on the market that are intended for self-administration. These devices have different degrees of functionality and thus complexity both regarding number of interacting components and handling of the actual device for delivering a dose of medicament.

In order that the patient or user is alerted regarding the state of the device for example regarding the number of doses that have been delivered or are remaining as well as the dose size, if the user may set different dose sizes, some devices are arranged with indicia visible through openings or windows in the device for mechanical dose information mechanisms or electronic displays if the device is provided with electronic dose information mechanisms.

Regarding mechanical dose information mechanisms, indicia are often arranged on an outer surface of a rotatingly arranged member, which during dose setting and/or dose delivery rotates a certain amount, which is displayed in the opening or window of the device. This function is adequate for many devices where the doses are rather large and/or that the rotation of the dose information member is to such an extent that all the indicia to be shown can fit onto the surface of the member.

However, for some devices and in particular when the dose increments are rather small, or the movement of the indicia member is rather small for a set dose, all indicia to be shown cannot fit onto the surface of the member which leads to problem regarding providing the user with the appropriate information.

There is thus a need for improvement regarding electromechanical dose information mechanisms that can handle small dose increments such that the proper information is provided to the user, e.g. having some sort of transmission or the like in order to handle movement of components of a medicament delivery device.

WO2008037801 discloses an injection device having a dose setting mechanism comprising linear capacitive sensors. The measurement is performed by analogue capacitance measurements which are then converted to digital form. The means for electronically detecting the amount of a set dose and/or the means for electronically detecting the amount of an injected dose may comprise at least two substantially disc shaped members being arranged with a substantially fixed mutual distance along a longitudinal direction of the injection device, said substantially disc shaped members being rotationally movable relatively to each other during dose setting and/or injection, and an angular displacement between said substantially disc shaped members may in this case be indicative of the amount of a set dose and/or the amount of an injected dose.

WO2007116090 discloses an injector having a complex dose setting mechanism comprising several electrodes on the outer surface of a dose indication barrel connected to contact members of an electronic device, and wherein said contact members are arranged to be slide across said electrodes when said barrel is rotated.

WO2007141225 discloses a medication delivery device having a dose setting mechanism which comprises first and second transmitter electrodes and a receiver electrode positioned on the inner surface of a housing and an axially movably member having a reflector electrode, wherein the reflector electrode is adapted to be capacitive coupled to at least one of the transmitter electrodes and to the receiver electrode, such that when said transmitter electrodes are provided with transmitter signals the axial position of the movably member is detected by the receiver electrode. The measurement is performed by analogue capacitance measurements which are then converted to digital form.

US2004135078 discloses a medication delivery device having a dose setting mechanism with an optical sensor.

BRIEF DESCRIPTION OF THE INVENTION

The aim of the present invention is to remedy the drawbacks of the state of the art devices and to provide a medicament delivery device having an electromechanical dose setting mechanism capable of handling and displaying dose information in a wide range of dose quantities.

This aim is obtained by the features of the independent patent claim.

According to a main aspect of the invention it is characterised by a medicament delivery device comprising a generally elongated housing comprising a distal and a proximal housing part having opposite distal and proximal ends; a medicament container coaxially arranged within said proximal housing part; drive means arranged to act on said medicament container for expelling a dose of medicament; and an electromechanical dose setting mechanism interactively connected to said drive means; wherein said electromechanical dose setting mechanism comprises a manually operable dose setting button; a dose setting member comprising sensors and arranged to be linearly displaced a predetermined distance along a linear path when the dose setting button is manually operated; and a printed circuit board having a code sensing area along the linear path of movement of the sensors, and wherein the sensors are arranged adjacent said code sensing area, such that a value of the immediate position of the dose setting member is determined and displayed as a dose value by electronic components on the printed circuit board.

Further aspects of the invention form the subject of the dependent patent claims.

Even though the above mentioned devices have proved to function well and display a high degree of user-friendliness, there is always a desire for improvements of such devices, among them being the design of the dose setting mechanism in order to simplify the manufacture and assembly in order to reduce costs but at the same time maintain or even improve the reliability of the function of the device.

These and other aspects of and advantages with the present invention will become apparent from the following detailed description and from the accompanying drawings.

BRIEF DESCRIPTION OF THE DRAWINGS

In the following detailed description of the invention, reference will be made to the accompanying drawings, of which

DETAILED DESCRIPTION OF THE INVENTION

Figure 1:
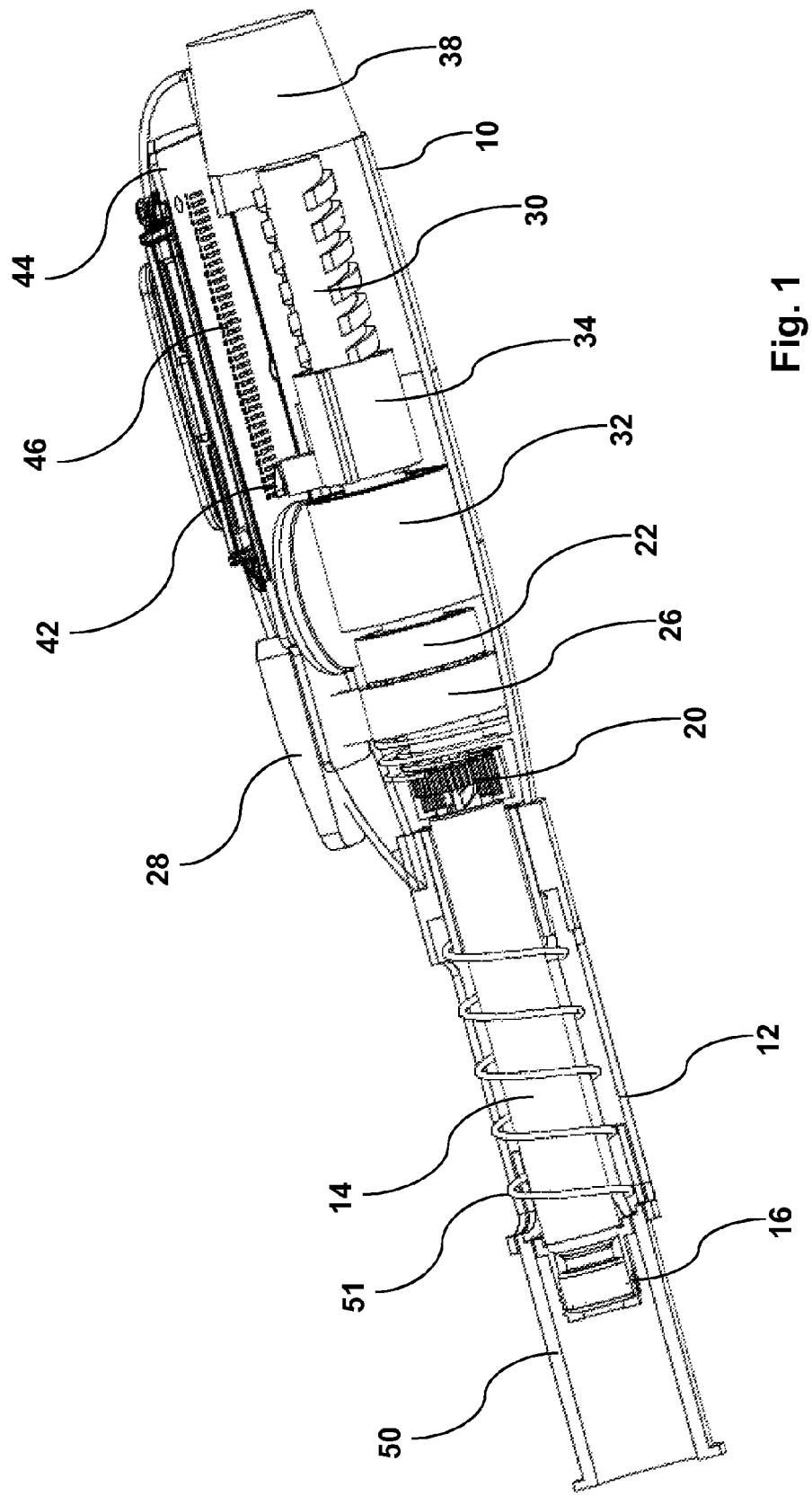
FIG. 1 shows a perspective view of the medicament delivery device according to the present invention wherein a longitudinal part of the housing has been removed.

In the present application, when the term "distal part/end" is used, this refers to the part/end of a medicament delivery device, or the parts/ends of the members thereof, which under use of the device is located the furthest away from a medicament delivery site of a patient. Correspondingly, when the term "proximal part/end" is used, this refers to the part/end of the device, or the parts/ends of the members thereof, which under use of the device is located closest to the medicament delivery site of the patient.

The medicament delivery device shown in the drawings and comprising the present invention comprises:
- a generally elongated housing comprising a distal 10 and a proximal 12 housing part having opposite distal and proximal ends;
- a medicament container 14 coaxially arranged within said proximal housing part;
- drive means arranged to act on said medicament container for expelling a dose of medicament; and
- an electromechanical dose setting mechanism interactively connected to said drive means; wherein said electromechanical dose setting mechanism comprises:
- a manually operable dose setting button 38;
- a dose setting member 34 comprising sensors 42 and arranged to be linearly displaced a predetermined distance along a linear path when the dose setting button 38 is manually operated; and
- a printed circuit board 44 having a code sensing area 46 along the linear path of movement of the sensors, and wherein the sensors are arranged adjacent said code sensing area, such that a value of the immediate position of the dose setting member 34 is determined and displayed as a dose value by electronic components on the printed circuit board.

In one example of the present invention shown in FIG. 1, the proximal housing part 12 is arranged as a medicament container holder 12 which is releasibly attached to the distal housing part by a suitable engagement means as threads, bayonets or the like. The medicament container 14 is arranged inside the proximal housing part. The proximal end of the proximal housing part is arranged with a neck 16 having suitable engagement means as threads, bayonets or the like, onto which a medicament delivery member as a needle, a mouthpiece or the like, not shown, may be attached.

The drive means comprises a threaded plunger rod 18 having a proximal end abutting a stopper (not shown) within a the medicament container; a rotational locking member 20 interactively connected to the plunger rod; a nut 22 threadedly arranged to the plunger rod, a locking member 23 interactively connected to the rotational locking member; a driver 30 threadedly connected to said dose setting member and wherein the proximal end of the driver is releasibly attached to the nut, and the distal end of the driver is fixedly connected to the manually operable dose setting button 38; and a force means 32 having a first end connected to the driver and a second end connected to a fix point on the distal housing part.

Figure 2:
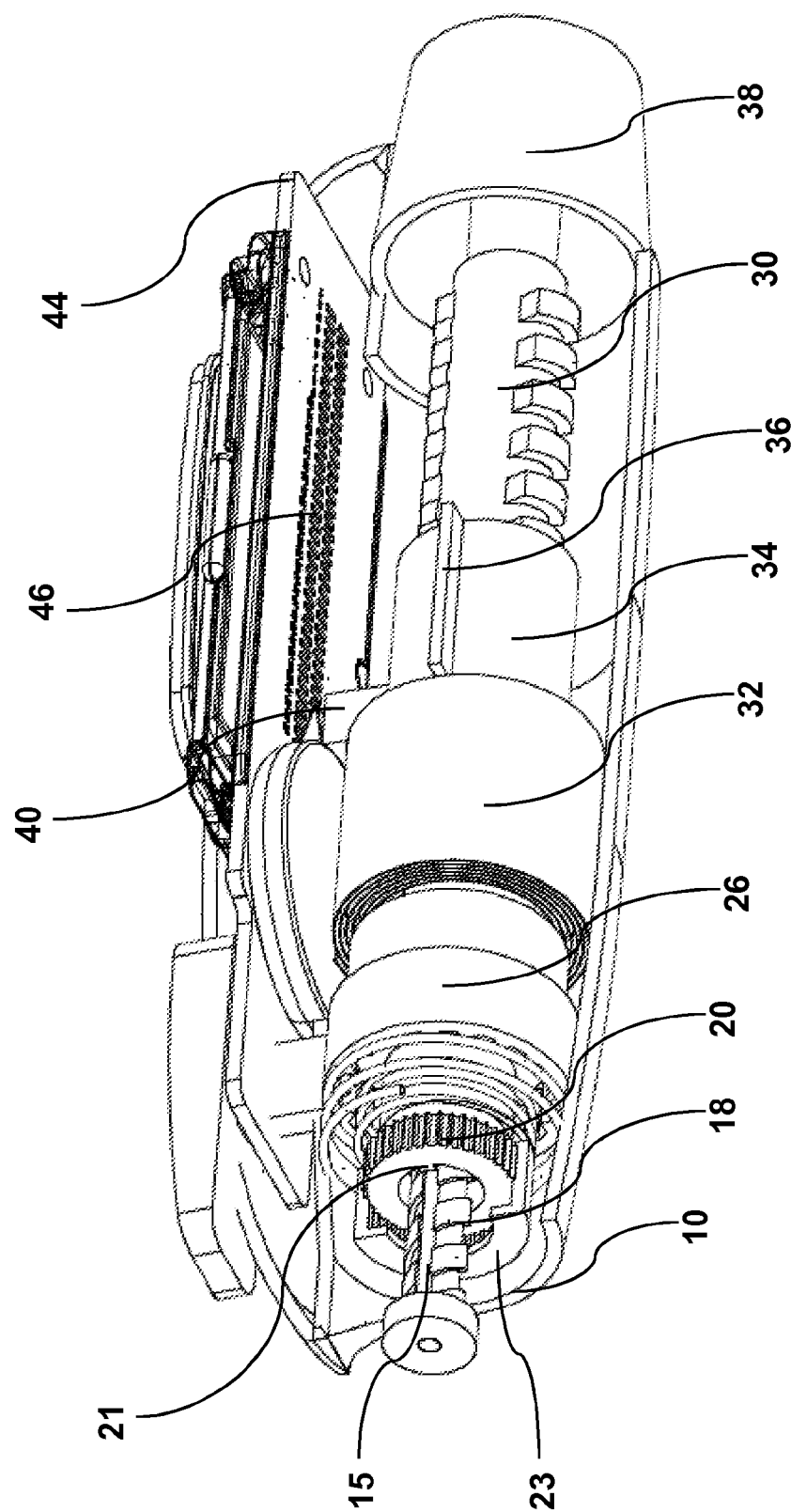
FIG. 2 shows a perspective view of the distal part of medicament delivery device of FIG. 1.
Figure 3:
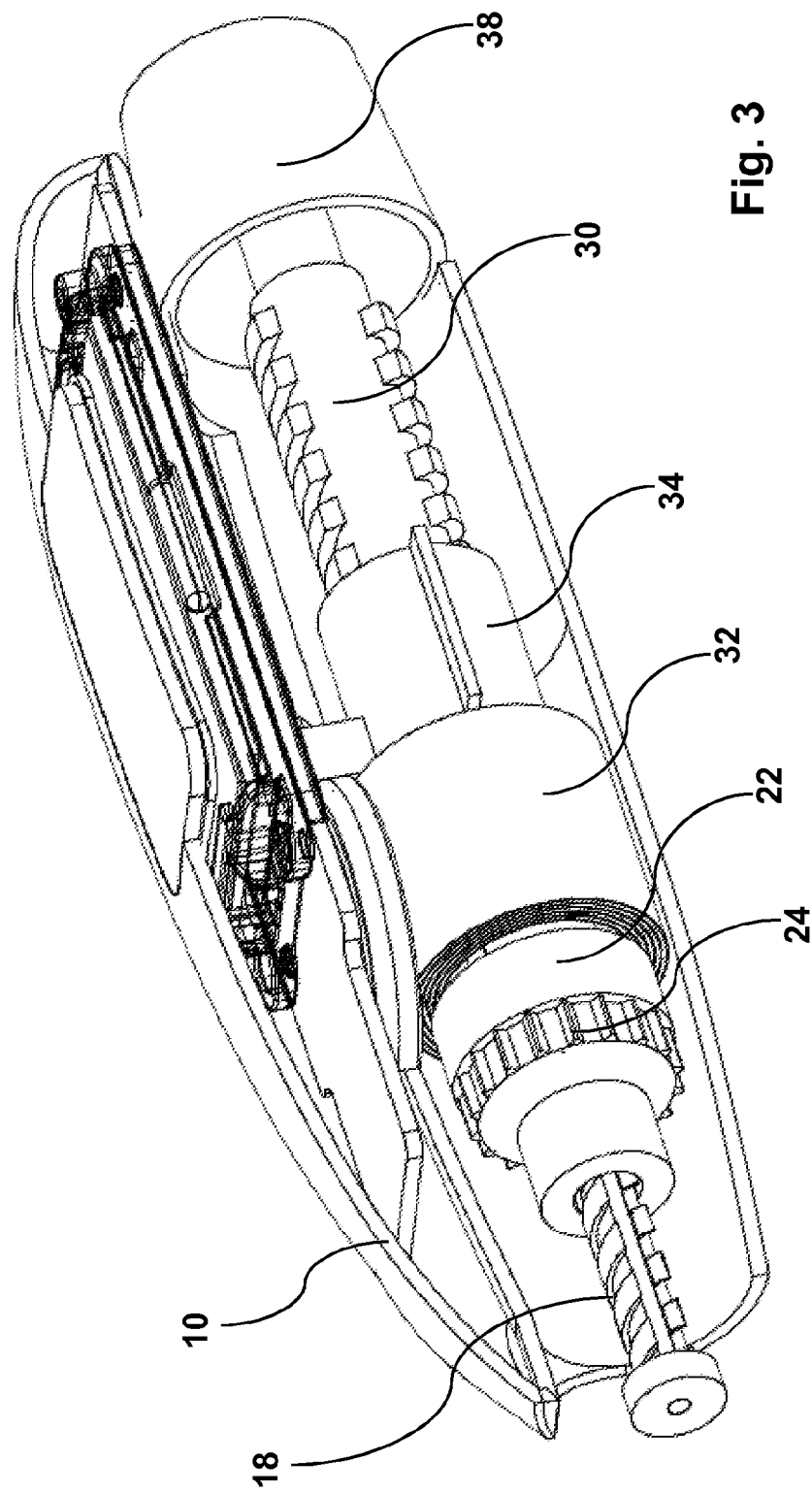
FIG. 3 shows a perspective view of a distal part of the medicament delivery device of FIG. 1 wherein the circular locking member 26, the rotational locking member 20, and the locking member 23 have been removed.
Figure 4:
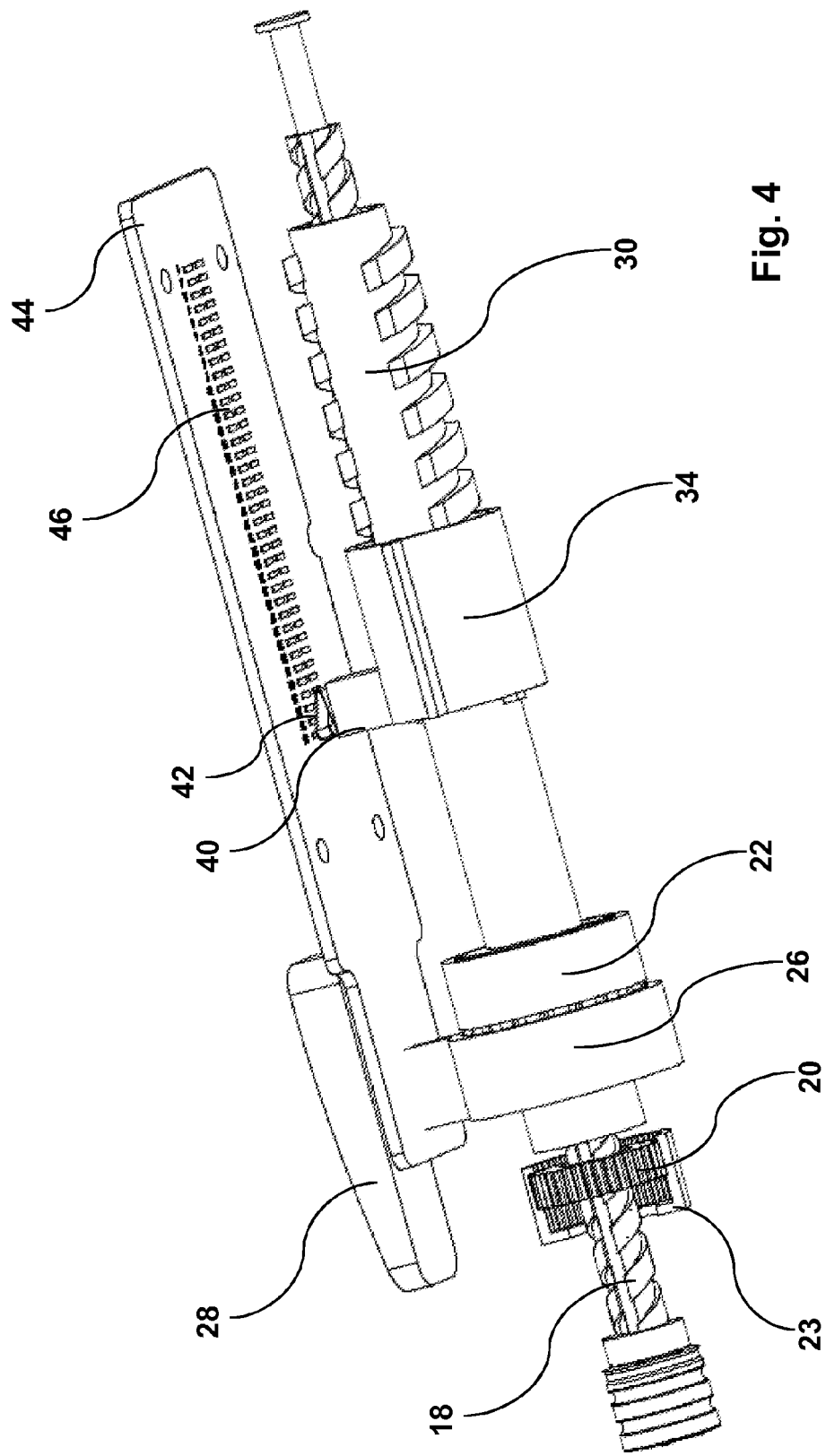
FIG. 4 shows a perspective view of a distal part of the medicament delivery device of FIG. 1 wherein the distal housing part 10, and the manually operable dose setting button 38 have been removed.

The plunger rod 18 extends axially through the rotational locking member 20 which is arranged with radial inwardly protrusions 21 which fit into longitudinal grooves 15 on the plunger rod, FIG. 2, as to provide a lock against rotation of the plunger rod in relation to the driver 30 and the nut 22, as it will be explained below. The rotational locking member 20 is arranged with a circumferential surface, which surface is arranged with a ratchet that interacts with the locking member 23. The nut 22 is threaded onto the plunger rod and is arranged with an outer circumferential surface, FIG. 3, which surface is arranged with teeth 24 that interact with corresponding teeth of a circular locking member 26 slidable arranged in relation to the nut 22. The circular locking member is arranged with a button 28 protruding through an opening on the distal housing part 10. Further, the driver 30, having the shape of an elongated tube inside which the plunger rod extends, is releasibly attached to said nut and arranged with threads on its outer surface. The force means 32 such as a spring drive member is coaxially arranged on the driver 30 and connected with a first end to the driver 30 and with a second end to a fix point on the distal housing part 10.

The locking member 23 of the example shown in the FIGS. 1-4, is slidably attached to the distal housing part, but may also be a resilient tongue on the proximal end of the distal housing part. Said locking member being adapted to interact with the distal end of the proximal housing part when said proximal housing part and said distal housing part are attached to each other.

The dose setting member 34 having a tubular shaped is arranged surrounding the driver and arranged with corresponding threads on its inner surface. On its outer surface, guide means 36 are arranged, which cooperate with grooves on the inner surface of the distal housing part for preventing rotation of the dose setting member but allowing linear movement of the dose setting member. The distal end of the driver 30 is fixedly connected to the manually operable dose setting button 38, capable of turning the driver. The dose setting member 34 is further arranged with a support 40 protruding radially outwards from the outer circumferential surface of said dose setting member. On the end surface of the support, a number of sensors 42 are arranged, preferably positioned side by side as seen in the longitudinal direction of the device. The sensors are in contact with a flat surface of the printed circuit board 44. The surface is arranged with a code sensing area 46 having a code that will be described below. The printed circuit board is further arranged with electronic components as processors, memory means, I/O devices and displays for performing different functions and handling different signals.

When the device is of an injection type as shown in the figures, the device may further comprise a needle shield sleeve 50 coaxially arranged within the proximal housing part 12. The proximal end of the needle shield sleeve protrudes through the proximal end of the proximal housing part and is held in this position due to a force exerted on the distal end of the needle shield sleeve by a needle shield spring 51 which is coaxially arranged inside the needle shield sleeve, FIG. 1.

The device is intended to function as follows. When a dose is to be delivered by the device the manually operable dose setting button 38 is turned. The dose setting member 34 is initially in a foremost proximal position, which is indicated by the interaction between the sensors 42, the code sensing area 46, and the electronic components in the printed circuit board, as the zero position. When the dose knob is rotated, so is the driver 30 due to the connection between them. The threads of the driver 30 cooperating with the dose setting member 34 causes the latter to move axially towards the distal end of the device, prevented from rotating by the guide means 36. The linear movement of the dose setting member 34 causes the sensors 42 to move over the codes of the sensing area 46, whereby values of the immediate positions are detected, i.e. the actual values from the zero value. The codes can be different variants of Grey codes, binary codes and the like. In this manner the electronics always knows the exact location of the dose setting member 34 in relation to the zero or reset position. The turning of the manually operable dose setting button 38 also causes the force means 32 to be tensioned. When the desired dose quantity is set, the device is ready for delivery.

When the device is of an injection type as shown in the figures, the user presses the needle shield sleeve against an injection site whereby the needle shield sleeve moves towards the distal end of the device compressing the needle shield spring 51. At the same time a needle (not shown), which has been attached to the neck 16 of the proximal housing part 12, penetrates the injection site. Then, the button 28 is actuated causing the teeth of the circular locking member 26 to move out of contact with the teeth 24 of the nut 22, which then is free to rotate because of the force of the force means 32. The rotation of the nut 22 causes the plunger rod 18 to move forward linearly and to expel a dose of medicament due to the threaded connection between the nut and the plunger rod as well as the rotational lock of the plunger rod with the rotational locking member 20.

During the rotation of the nut 22, the driver 30 is also rotated, whereby the dose setting member 34 is moved linearly back to the initial position, terminating the medicament delivery sequence. During this movement the sensors 42 move over the sensing area 46, constantly sensing the actual position of the drive member in relation to the zero position. In this aspect it is to be understood that the distance that the dose setting member is moved back to its initial position corresponds to the distance the plunger rod and thus the stopper are moved inside the medicament container.

As is apparent from the above, a number of different sensor technologies may used in order to detect the absolute values of the position of the dose setting member, including capacitive, resistive, optical, mechanical, electro-mechanical technologies and combinations of these. The number of sensors as well as the design ad patterns of the sensing areas may be modified in many ways in order to obtain the desired function. In this aspect the key features of the invention are that the movement is linear and that absolute values are obtained from the device.

It is to be understood that the embodiments described above and shown in the drawings only are to be regarded as non-limiting examples of the invention and that it may be modified in many ways within the scope of the patent claims.

The invention claimed is:

1. A medicament delivery device, comprising:
  a generally elongated housing having distal and proximal housing parts having opposite distal and proximal ends;
  a medicament container coaxially arranged within the proximal housing part;
  a drive mechanism arranged to act on the medicament container for expelling a dose of medicament; and
  an electromechanical dose setting mechanism interactively connected to the drive mechanism, wherein the electromechanical dose setting mechanism includes:
    a manually operable dose setting button;
    a dose setting member that includes sensors arranged to be linearly displaced a predetermined distance along a linear path when the dose setting button is manually operated; and
    a printed circuit board that has a code sensing area having a code along the linear path of the sensors, wherein the sensors are arranged adjacent the code sensing area such that a value of an immediate position of the dose setting member is determined and displayed as a dose value by electronic components on the printed circuit board;
  wherein the drive mechanism includes:
    a threaded plunger rod having a proximal end abutting a stopper within the medicament container;
    a rotational locking member interactively connected to the plunger rod;
    a nut threadedly arranged to the plunger rod, a locking member interactively connected to the rotational locking member,
    a driver having a shape of an elongated tube, inside which the plunger rod extends; the driver being releasably attached to the nut; and the driver being arranged with threads on its outer surface; and
    a force mechanism having a first end connected to the driver and a second end connected to a fixed point on the distal housing part; and
  the dose setting member has a tubular shape, is arranged surrounding the driver and with corresponding threads on its inner surface, and includes guide devices on its outer surface that cooperate with grooves on an inner surface of the distal housing part for preventing rotation of the dose setting member but allowing linear movement of the dose setting member; and
  the distal end of the driver is fixedly connected to the manually operable dose setting button, capable of turning the driver.

2. The medicament delivery device of claim 1, wherein the nut has an outer circumferential surface having teeth that interact with corresponding teeth of a circular locking member that is slidably arranged in relation to the nut; and the circular locking member includes a button protruding through an opening on the distal housing part.

3. The medicament delivery device of claim 1, wherein the electronic components of the printed circuit board include at least one of a processor, a memory, an input/output device, and a display.

4. The medicament delivery device of claim 1, wherein the plunger rod extends axially through the rotational locking member, which has radially inward protrusions that fit into longitudinal grooves on the plunger rod for providing a lock against rotation of the plunger rod in relation to the nut; and the rotational locking member has a circumferential surface having a ratchet that interacts with the locking member.

5. The medicament delivery device of claim 4, wherein the electronic components of the printed circuit board include at least one of a processor, a memory, an input/output device, and a display.

6. The medicament delivery device of claim 4, wherein the nut has an outer circumferential surface having teeth that interact with corresponding teeth of a circular locking member that is slidably arranged in relation to the nut; and the circular locking member includes a button protruding through an opening on the distal housing part.

7. The medicament delivery device of claim 6, wherein the electronic components of the printed circuit board include at least one of a processor, a memory, an input/output device, and a display.

* * * * *